(12) United States Patent
Tsuji et al.

(10) Patent No.: US 10,107,792 B2
(45) Date of Patent: Oct. 23, 2018

(54) CELL POTENTIAL MEASURING ELECTRODE ASSEMBLY AND METHOD FOR MEASURING ELECTRIC POTENTIAL CHANGE OF CELL USING THE SAME

(71) Applicant: Panasonic Corporation, Osaka (JP)

(72) Inventors: Kiyotaka Tsuji, Osaka (JP); Ken Shimono, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 297 days.

(21) Appl. No.: 15/047,619

(22) Filed: Feb. 18, 2016

(65) Prior Publication Data
US 2016/0320365 A1 Nov. 3, 2016

(30) Foreign Application Priority Data
Apr. 28, 2015 (JP) .................................. 2015-091020

(51) Int. Cl.
*G01N 27/327* (2006.01)
*G01N 33/487* (2006.01)
*G01N 33/483* (2006.01)

(52) U.S. Cl.
CPC ... *G01N 33/48728* (2013.01); *G01N 33/4836* (2013.01)

(58) Field of Classification Search
CPC ........................ G01N 33/4833; G01N 33/4836
See application file for complete search history.

(56) References Cited

U.S. PATENT DOCUMENTS

| 6,132,683 A | 10/2000 | Sugihara et al. |
| 8,052,932 B2 | 11/2011 | Han et al. |
| 2010/0270176 A1* | 10/2010 | Xiang ............... B01L 3/502707 205/777.5 |
| 2016/0270729 A1* | 9/2016 | Dvir ..................... C12N 5/0068 |

OTHER PUBLICATIONS

Bursac et al., "Cardiomyocyte Cultures with Controlled Macroscopic Anisotropy," Circulation Research, published online Nov. 14, 2002 (Year: 2002).*
Xinhua Zong et al., "Electrospun fine-textured scaffolds for heart tissue constructs", Biomaterials 26 (2005) 5330-5338.
Yuliya Orlova et al., "Electrospun nanofibers as a tool for architecture control in engineered cardiac tissue", Biomaterials 32 (2011) 5615-5624.

* cited by examiner

*Primary Examiner* — Alexander S Noguerola
(74) *Attorney, Agent, or Firm* — McDermott Will & Emery LLP

(57) ABSTRACT

The present invention provides a cell potential measuring electrode assembly comprising: an insulating substrate; a conductive pattern arranged in the insulating substrate; an insulating fiber having cell compatibility; and a measurement electrode. The insulating fiber is arranged on the insulating substrate. The measurement electrode has a front surface and a back surface. The back surface of the measurement electrode is in contact with the conductive pattern. The insulating fiber is not arranged on the front surface of the measurement electrode. The cell potential measuring electrode assembly according to the present invention has low impedance. The cell potential measuring electrode assembly according to the present invention is suitable to measure electric potential change of a cardiomyocyte.

33 Claims, 18 Drawing Sheets

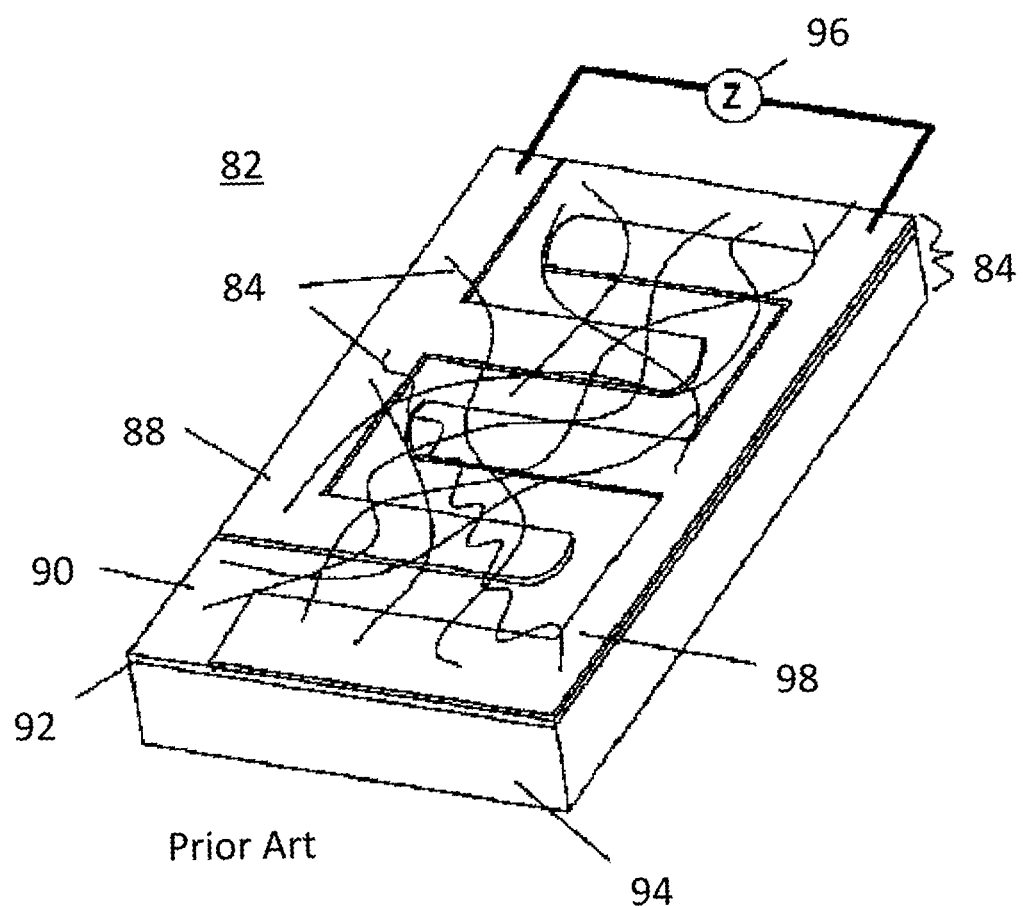
Prior Art
FIG. 18
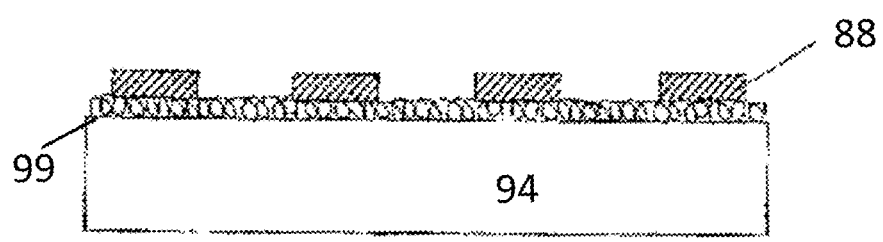
Prior Art      FIG. 19

CELL POTENTIAL MEASURING ELECTRODE ASSEMBLY AND METHOD FOR MEASURING ELECTRIC POTENTIAL CHANGE OF CELL USING THE SAME

BACKGROUND

1. Technical Field

The present invention relates to a cell potential measuring electrode assembly and a method for measuring electric potential change of a cell using the same.

2. Description of the Related Art

U.S. Pat. No. 6,132,683 discloses a low impedance cell potential measuring electrode assembly. FIG. 17 shows the low impedance cell potential measuring electrode assembly disclosed in U.S. Pat. No. 6,132,683. This low impedance cell potential measuring electrode assembly typically has a number of microelectrodes on an insulating substrate and has a wall enclosing the region including the microelectrodes. The device is capable of measuring electrophysiological activities of a monitored sample using the microelectrodes while cultivating cells or tissues of the sample in the region of the microelectrodes. In U.S. Pat. No. 6,132,683, independent reference electrodes are utilized to lower the impedance of the overall system and to therefore lower the noise often inherent in the measured data. Optimally the microelectrodes are enclosed by a physical wall used for controlling the atmosphere around the monitored sample.

U.S. Pat. No. 8,052,932 discloses a chemical sensor, a system, and a method for sensing a chemical species. FIG. 18 is a duplicate of FIG. 1 included in U.S. Pat. No. 8,052,932. As shown in FIG. 18, the chemical sensor 82 disclosed in U.S. Pat. No. 8,052,932 comprises a fiber mat 84, a substrate 86, an electrode 88, an insulating surface 90, an insulator 92, and a wafer 94. FIG. 19 is a duplicate of FIG. 3D included in U.S. Pat. No. 8,052,932. As shown in FIG. 19, composite nanofiber sensing material 99a is stacked on the substrate 94 (i.e., on the wafer 94). The printed electrode 88 is formed on the composite nanofiber sensing material 99a.

SUMMARY

The present invention provides a cell potential measuring electrode assembly comprising:
an insulating substrate;
a conductive pattern arranged in the insulating substrate;
an insulating fiber having cell compatibility; and
a measurement electrode,
wherein
the insulating fiber is arranged on the insulating substrate;
the measurement electrode has a front surface and a back surface;
the back surface of the measurement electrode is in contact with the conductive pattern; and
the insulating fiber is not arranged on the front surface of the measurement electrode.

The cell potential measuring electrode assembly according to the present invention has low impedance. The cell potential measuring electrode assembly according to the present invention is suitable to measure electric potential change of a cardiomyocyte.

BRIEF DESCRIPTION OF THE DRAWINGS

FIG. 18 is a duplicate of FIG. 1 included in U.S. Pat. No. 8,052,932.

FIG. 19 is a duplicate of FIG. 3D included in U.S. Pat. No. 8,052,932.

DETAILED DESCRIPTION OF THE EMBODIMENT

Hereinafter, the embodiment of the present invention will be described with reference to the drawings.

Cell Potential Measuring Electrode Assembly 100

Figure 1:
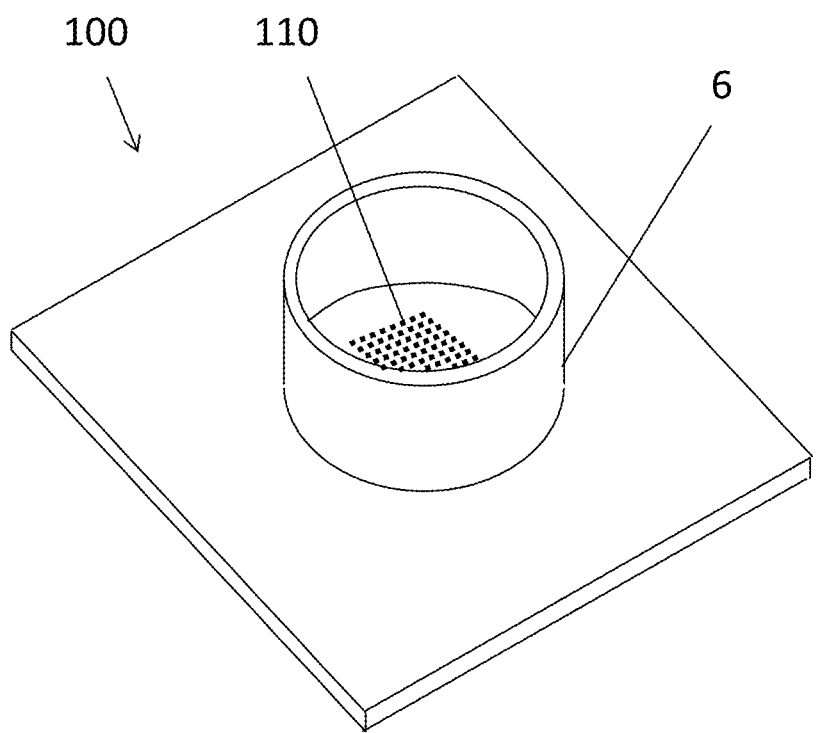
FIG. 1 shows a schematic view of a cell potential measuring electrode assembly 100 according to an embodiment.

FIG. 1 shows a schematic view of the cell potential measuring electrode assembly 100 according to the present embodiment. The cell potential measuring electrode assembly 100 comprises a first fence such as a cylindrical member 6, as shown in FIG. 1. A plurality of measurement electrodes 110 are arranged in the cylindrical member 6.

Figure 2:
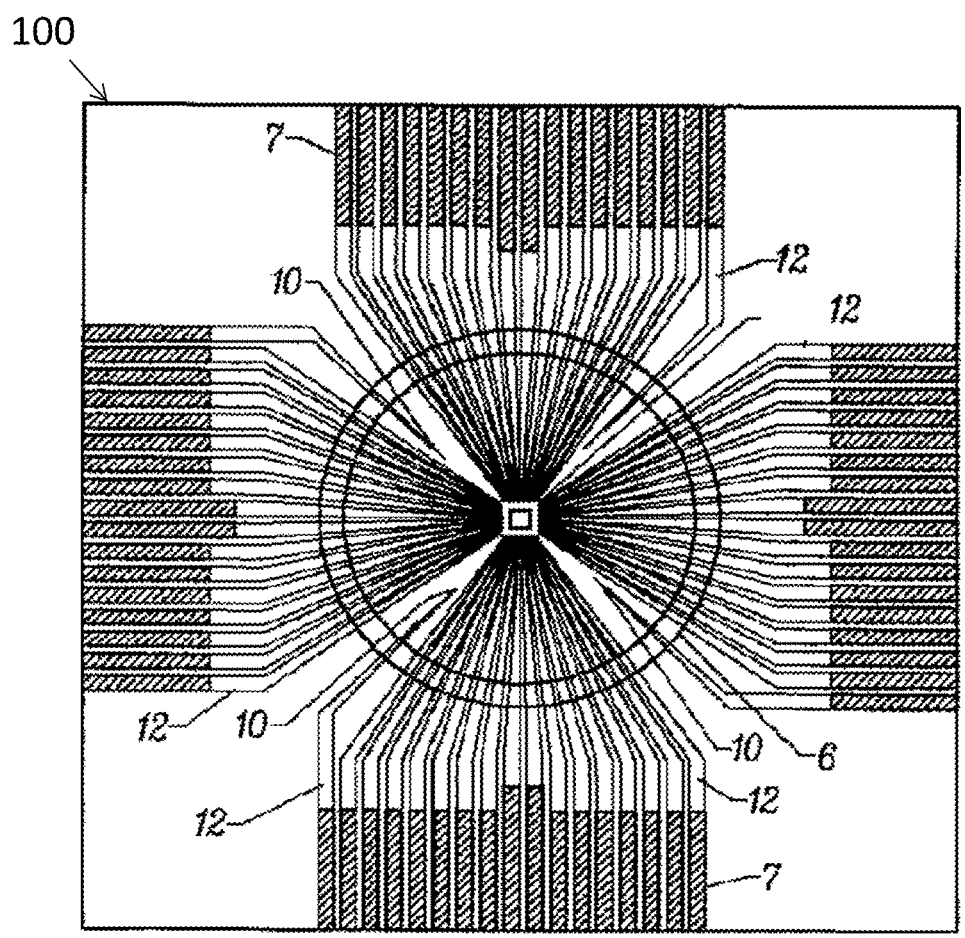
FIG. 2 shows a top view of the cell potential measuring electrode assembly 100.

FIG. 2 shows a top view of the cell potential measuring electrode assembly 100. The cell potential measuring electrode assembly 100 has a plurality of electrodes 7 and a plurality of conductive patterns 12 in the outside of the cylindrical member 6, as shown in FIG. 2. Each electrode 7 is connected to one end of one of the conductive patterns 12. Among these electrodes 7, some of the electrodes 7 function as reference electrodes 10. Each of the other ends of the conductive patterns 12 connected to the remaining electrodes 7 is connected to each of the measurement electrodes 110 in the inside of the cylindrical member 6. In FIG. 1, the electrodes 7, the reference electrodes 10 and the conductive patterns 12 are omitted. In FIG. 2, the measurement electrodes 110 are omitted.

Figure 3A:
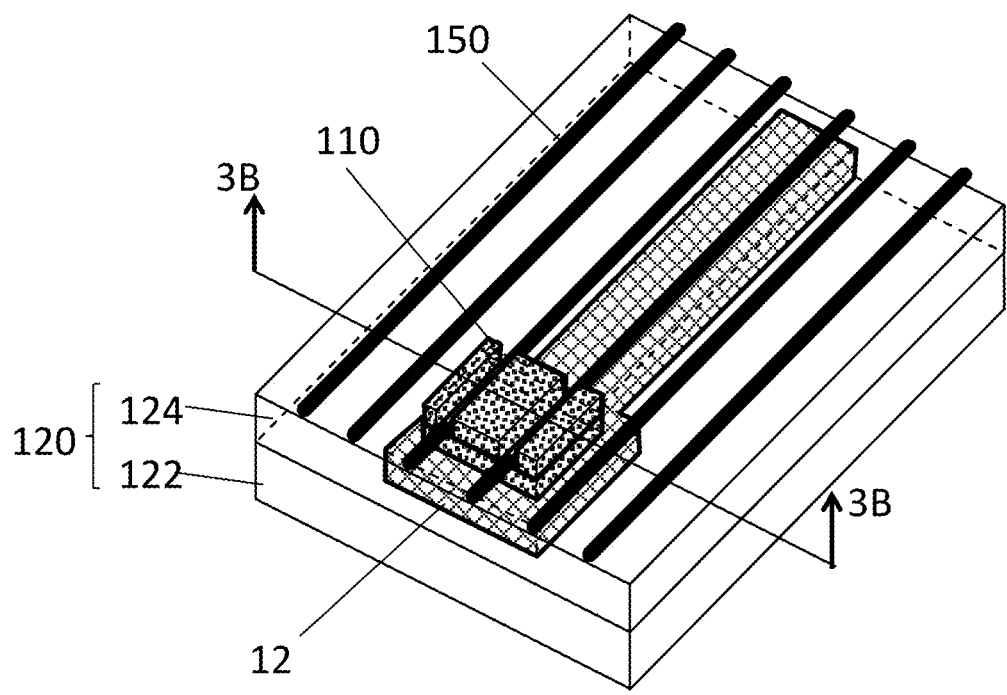
FIG. 3A shows a schematic view of one measurement electrode 110 included in the cell potential measuring electrode assembly 100.
Figure 3B:
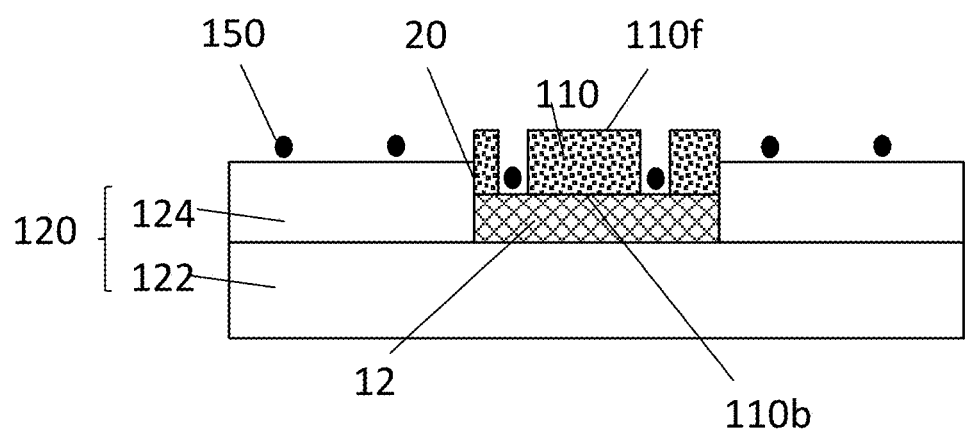
FIG. 3B shows a cross-sectional view taken along the line 3B-3B included in FIG. 3A.

FIG. 3A shows a schematic view of one measurement electrode 110 included in the cell potential measuring electrode assembly 100. FIG. 3B shows a cross-sectional view taken along the line 3B-3B included in FIG. 3A. The cell potential measuring electrode assembly 100 comprises an insulating substrate 120, a conductive pattern 12, an insulating fiber 150 and a measurement electrode 110, as shown in FIG. 3A and FIG. 3B.

Insulating Substrate 120

The insulating substrate 120 may comprise a first substrate 122 and a second substrate 124. Both the first substrate 122 and the second substrate 124 are electrically insulative. The second substrate 124 is stacked on the first substrate 122. In FIG. 3A and FIG. 3B, the insulating substrate 120 is composed of the first substrate 122 and the second substrate 124.

Conductive Pattern 12

The material of the conductive pattern 12 is not limited. As one example, the material of the conductive pattern 12 is indium tin oxide.

Hereinafter, described in detail is the case where the insulating substrate 120 comprises the first substrate 122 and the second substrate 124, as shown in FIG. 3A and FIG. 3B. The first substrate 122 has a front surface and a back surface. Similarly, the second substrate 124 also has a front surface and a back surface. The back surface of the second substrate 124 adheres to the front surface of first substrate 122. The conductive pattern 12 is formed on the front surface of the first substrate 122. The insulating fiber 150 is arranged on the front surface of the second substrate 124.

The second substrate 124 has a through-hole 20. A part of the measurement electrode 110 is embedded in the inside of the through-hole 20. The other part of the measurement electrode 110 projects upwardly from the through-hole 20. In other words, the other part of the measurement electrode 110 bulges from the surface of the second substrate 124. The measurement electrode 110 is electrically connected to the conductive pattern 12 at the bottom of the through-hole 20. In other words, a part of the conductive pattern 12 is exposed at the bottom of the through-hole 20, if the measurement electrode 110 is removed. As is clear from FIG. 3B, when a cell is arranged on the second substrate 124, the cell is not electrically connected to the conductive pattern 12. The cell is electrically connected only to the measurement electrode 110. This is because the second substrate 124 is insulative. It is desirable that the first substrate 122 is also insulative.

Insulating Fiber 150

The insulating fiber 150 is arranged on the insulating substrate 120. It is desirable that a plurality of the insulating fibers 150 are arranged on the insulating substrate 120. When the insulating substrate 120 comprises the first substrate 122 and the second substrate 124, it is desirable that the insulating fiber 150 is arranged on the front surface of the second substrate 124.

The insulating fiber 150 has cell compatibility. At the time of the measurement of the electric potential of the cell, the cell is arranged on the measurement electrode 110 so as to be in contact with the insulating fiber 150. When the cell is arranged on the insulating fiber 150 having cell compatibility, the cell is organized along the longitudinal direction of the insulating fiber 150. See the following documents (I) and (II).

(I) Xinhua Zong et al., "Electrospun fine-textured scaffolds for heart tissue constructs", Biomaterials 26 (2005) 5330-5338.

(II) Yuliya Orlova et al., "Electrospun nanofibers as a tool for architecture control in engineered cardiac tissue", Biomaterials 32 (2011) 5615-5624.

Figure 3C:
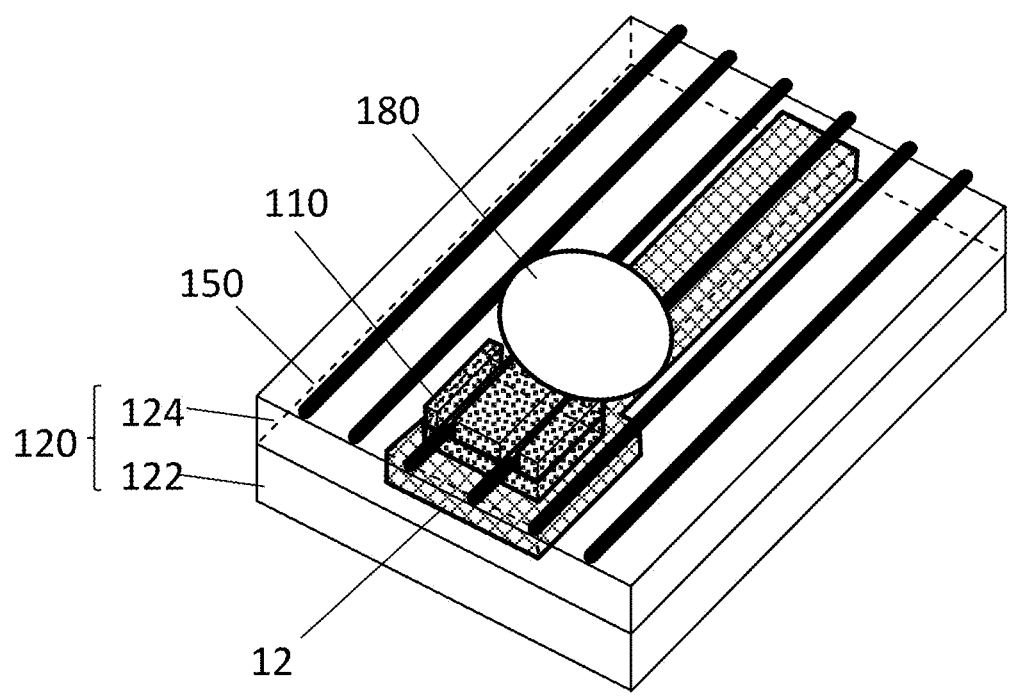
FIG. 3C shows a schematic view of the cell potential measuring electrode assembly 100 on which a cell 180 has been arranged.
Figure 3D:
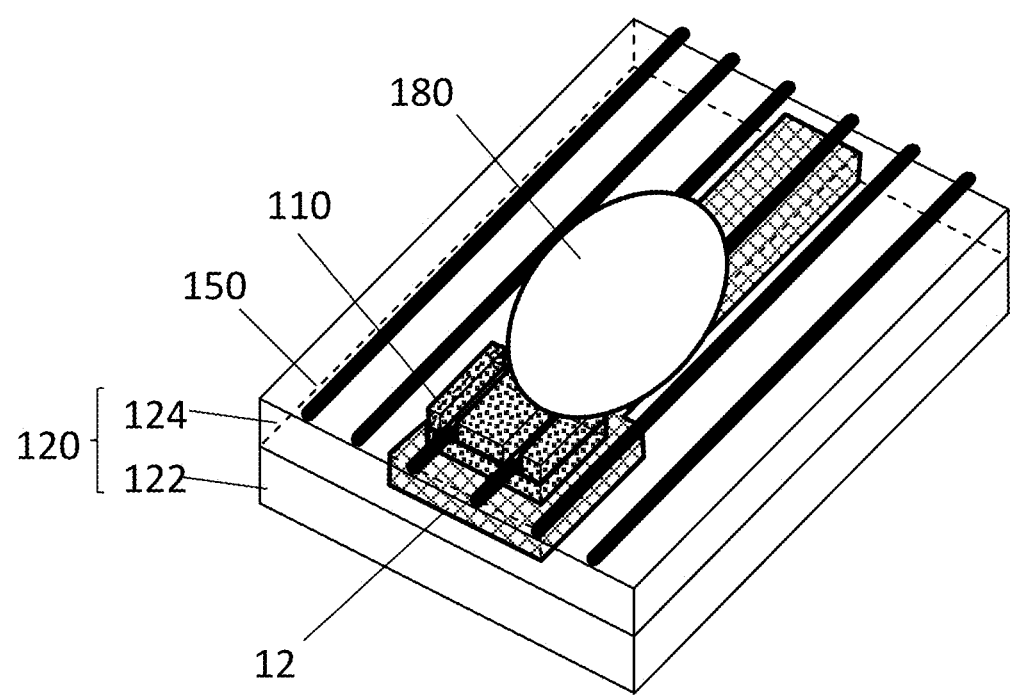
FIG. 3D shows a schematic view of the cell potential measuring electrode assembly 100 on which a cell 180 has been arranged.

In particular, in the present embodiment, as shown in FIG. 3C, when the cell 180 is arranged on the cell potential measuring electrode assembly 100 comprising such an insulating fiber 150, the cell 180 adsorbs onto the insulating fiber 150, and the cell 180 is spread so as to be extended along the longitudinal direction of the insulating fiber 150. See FIG. 3D.

An example of the cell used suitably in the present embodiment is a cardiomyocyte. It is well-known that a cardiomyocyte beats. The cardiomyocyte arranged on the insulating fiber 150 beats along the longitudinal direction of the insulating fiber 150. However, if the insulating fiber 150 is absent, the activity of the beat of the cardiomyocyte arranged on the insulating substrate is decreased. For this reason, the electric potential change of the cardiomyocyte is measured more appropriately in a case where the insulating fiber 150 is used than in a case where the insulating fiber 150 is absent. This is because the electric potential change of the cardiomyocyte is measured while the cardiomyocyte arranged on the insulating fiber 150 beats along the longitudinal direction of the insulating fiber 150.

It is desirable that the insulating fiber 150 is unfixed to the insulating substrate 120. The insulating fiber 150 fixed to the insulating substrate 120 may be a resistance for the beat of the cardiomyocyte. In other words, the fixed insulating fiber 150 may decrease the activity of the beat of the cardiomyocyte. It is desirable that the insulating fiber 150 is unfixed to the insulating substrate 120 to prevent the activity of the beat of the cardiomyocyte from being decreased.

The fiber 150 is required to be insulative. A conductive fiber has an adverse influence on the measurement of the electric potential change of the cell. For this reason, a carbon nanotube must not be used for the cell potential measuring electrode assembly 100 according to the present embodiment. Hereinafter, the reasons thereof will be described. A plurality of cells are arranged on the cell potential measuring electrode assembly 100 according to the present embodiment, as is described later. Among the plurality of the cells arranged in this way, the electric potential change of the cells located near the measurement electrode 110 is measured.

However, in case where the fiber 150 is conductive, since the plurality of the cells are electrically connected, the electric potential change of the cells located near the measurement electrode 110 is not measured.

An example of the material of the insulating fiber 150 having cell compatibility is polystyrene, polycarbonate, polymethylmethacrylate, polyvinyl chloride, polyethylene terephthalate, polyamide, polymethyl glutaric imide, or polylactic acid.

As shown in FIG. 3A and FIG. 3B, the insulating fiber 150 may be arranged on the conductive pattern 12 as well as on the insulating substrate 120 (e.g., on the second substrate 124). In other words, a part of one of the insulating fibers 150 may be located on the insulating substrate 120 (e.g., on the second substrate 124) and another part of the one of the insulating fibers 150 may be arranged on the conductive pattern 12.

In the above case, the insulating fiber 150 may be in contact not only with the conductive pattern 12 but also with the measurement electrode 110.

As shown in FIG. 3A and FIG. 3B, the cell potential measuring electrode assembly 100 according to the present embodiment may comprises a plurality of the insulating fibers 150. In FIG. 3A and FIG. 3B, six insulating fibers 150 are depicted. Two insulating fibers 150 located at the center are arranged not only on the second substrate 124 but also on the conductive pattern 12. The remaining four insulating fibers 150 are arranged on the second substrate 124.

As shown in FIG. 1 and FIG. 2, the cell potential measuring electrode assembly 100 according to the present embodiment may comprise a plurality of the conductive patterns 12 and a plurality of the measurement electrodes 110. In this case, the plurality of the insulating fibers 150 are used.

When the plurality of the insulating fibers 150 are used, as shown in FIG. 3A, it is desirable that each of the fibers is linear and that the plurality of the insulating fibers 150 are arranged along one direction. This is because, when the cardiomyocyte is used as the cell, the cardiomyocyte beats along the longitudinal direction of the plurality of the insulating fibers 150 arranged along the one direction.

Measurement Electrode 110

It is desirable that the measurement electrode 110 has a shape of a layer or a flat substrate. As shown in FIG. 3B, the measurement electrode 110 has a front surface 110f and a back surface 110b. The back surface 110b is in contact with the conductive pattern 12. For this reason, the measurement electrode 110 is electrically connected to the conductive pattern 12 through the back surface 110b. The front surface 110f is exposed.

Figure 4A:
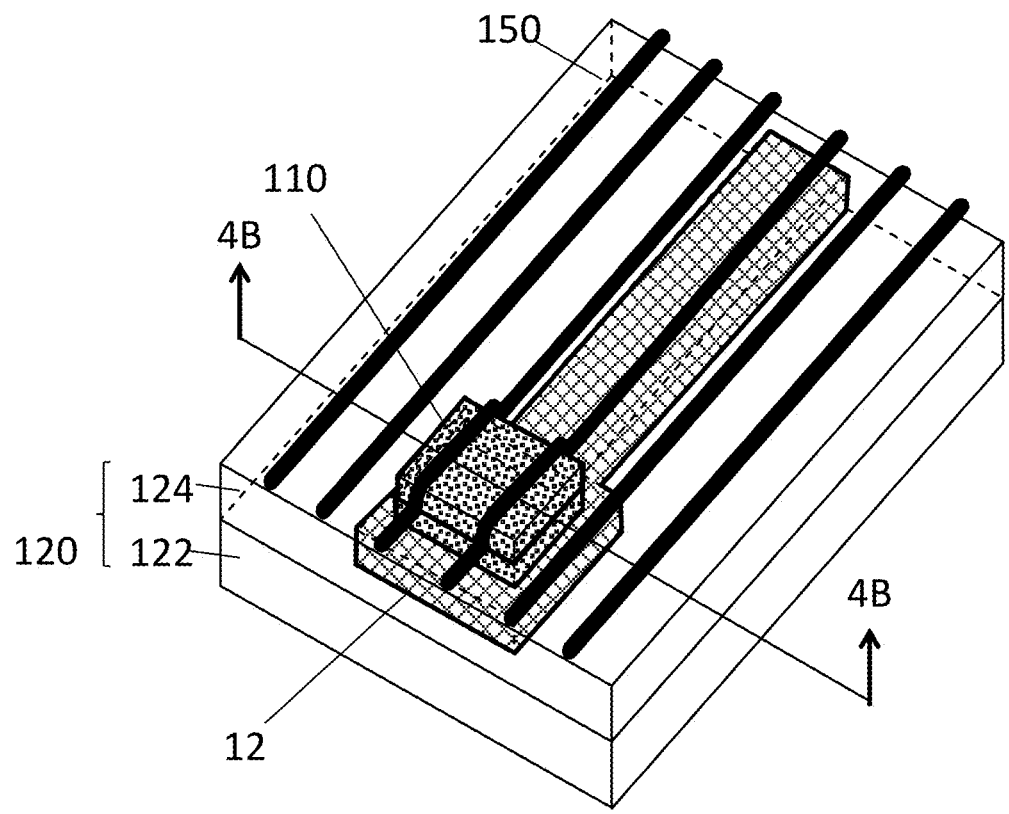
FIG. 4A shows a schematic view of one measurement electrode 110 included in a cell potential measuring electrode assembly 100 according to a comparative example.
Figure 4B:
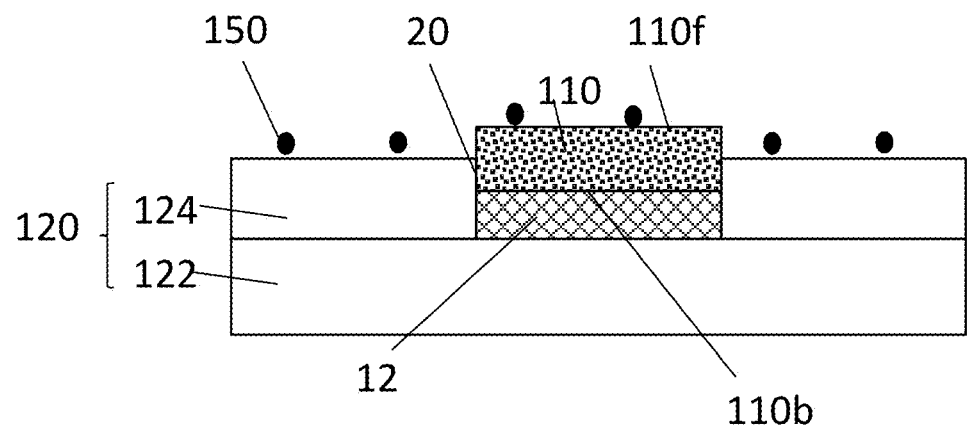
FIG. 4B shows a cross-sectional view taken along the line 4B-4B included in FIG. 4A.

In the present invention, the insulating fiber 150 must not be arranged on the front surface 110f of the measurement electrode 110. As shown in FIG. 4A and FIG. 4B, in case where the insulating fiber 150 is arranged on the front surface 110f of the measurement electrode 110, the cell potential measuring electrode assembly has high impedance, as demonstrated in the comparative example 1 which will be described later. As a result, a significantly high noise is generated during the measurement of the cell electrical potential, as demonstrated in the comparative example 2 which will be described later.

It is desirable that the measurement electrode 110 is a platinum electrode. The platinum electrode may be formed of platinum black.

Using Method

Next, a method for measuring the electric potential change of the cell using the cell potential measuring electrode assembly 100 will be described.

As shown in FIG. 2, it is desirable that the cell potential measuring electrode assembly 100 comprises a reference electrode 10. As shown in the cross-sectional view of FIG. 10, it is desirable that the measurement electrode 110 is arranged near the center of the cell potential measuring electrode assembly 100 and that the reference electrode 10 is arranged away from the center of the cell potential measuring electrode assembly 100. It is desirable that an insulating second fence such as an insulating ring 62 is arranged on the cell potential measuring electrode assembly 100 to separate the measurement electrode 110 from the reference electrode 10. A user of the cell potential measuring electrode assembly 100 prepares such a cell potential measuring electrode assembly 100. In other words, the user procures the cell potential measuring electrode assembly 100.

Figure 11:
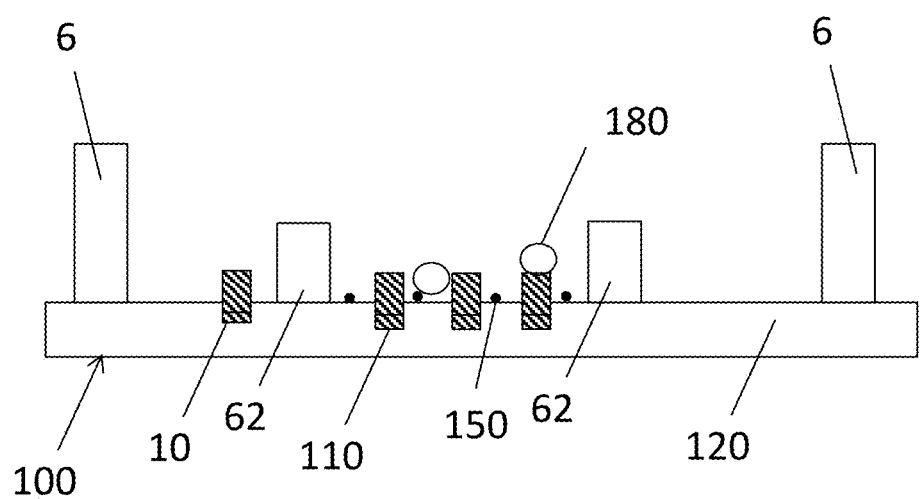
FIG. 11 shows a cross-sectional view of one step, subsequent to FIG. 10, included in the method for using the cell potential measuring electrode assembly 100.

As shown in FIG. 11, cells 180 are arranged on the insulating substrate 120 so as to be in contact with the measurement electrode 110 and the insulating fiber 150. After the cells 180 are arranged on the insulating substrate 120, it is desirable that the cells 180 are left at rest. In this way, the cells 180 mature on the insulating substrate 120 comprising the insulating fibers 150 on the surface thereof.

Figure 12:
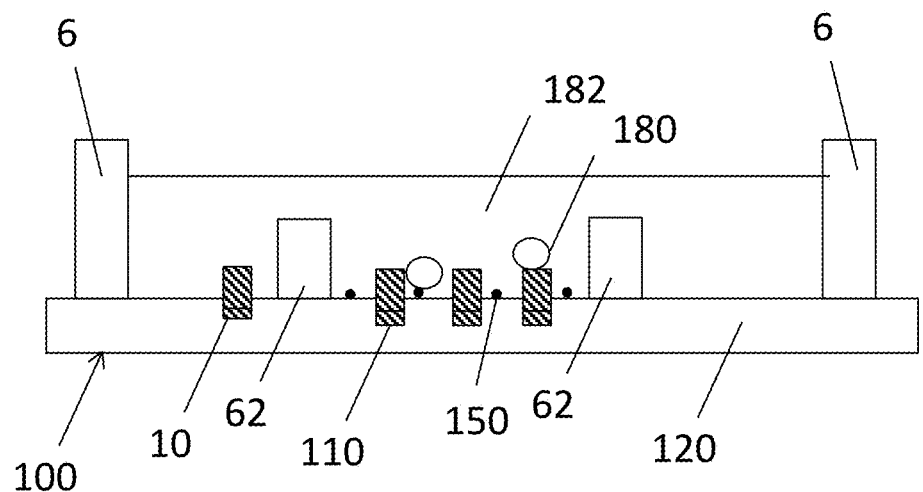
FIG. 12 shows a cross-sectional view of one step, subsequent to FIG. 11, included in the method for using the cell potential measuring electrode assembly 100.

Then, as shown in FIG. 12, a culture fluid 182 in contact with the cells 180 is supplied on the insulating substrate 120. Specifically, the culture fluid 182 is supplied to the chamber defined by the cylindrical member 6 and the insulating substrate 120. Finally, an electric potential difference between the reference electrode 10 and the measurement electrode 110 is measured as an electric potential change of the cells 180.

Figure 13:
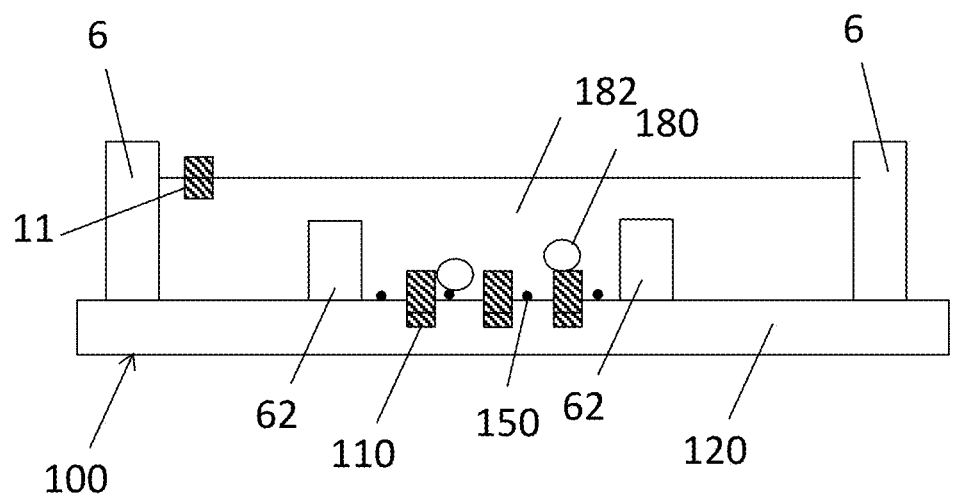
FIG. 13 shows a cross-sectional view of one step in place of the step shown in FIG. 12

If the cell potential measuring electrode assembly 100 does not comprise the reference electrode 10, as shown in FIG. 13, a reference electrode 11 is brought into contact with the culture fluid 182, after the culture fluid 182 is supplied to the chamber. In FIG. 13, a part of the reference electrode 11 is immersed in the culture fluid 182. However, all of the reference electrode 11 may be immersed in the culture fluid 182. In this way, at least one part of the reference electrode 11 is immersed in the culture fluid 182.

Then, similarly to the case shown in FIG. 12, an electric potential difference between the reference electrode 10 and the measurement electrode 110 is measured as an electric potential change of the cells 180.

Fabricating Method

Figure 8B:
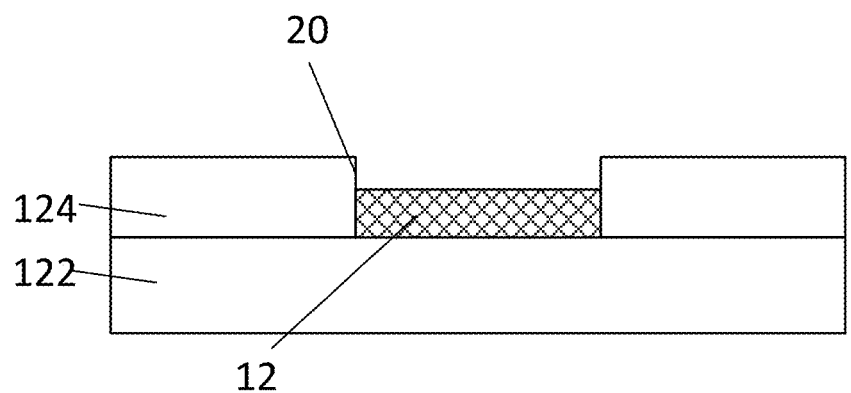
FIG. 8B shows a cross-sectional view taken along the line 8B-8B included in FIG. 8A.
Figure 9A:
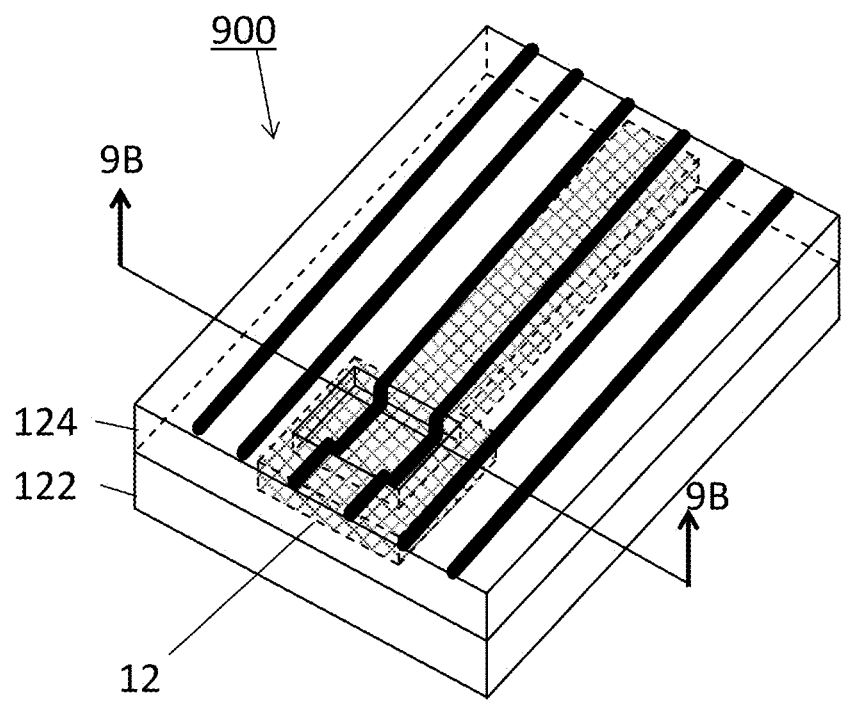
FIG. 9A shows a schematic view of one step, subsequent to FIG. 8A, included in the method for fabricating the cell potential measuring electrode assembly 100.
Figure 9B:
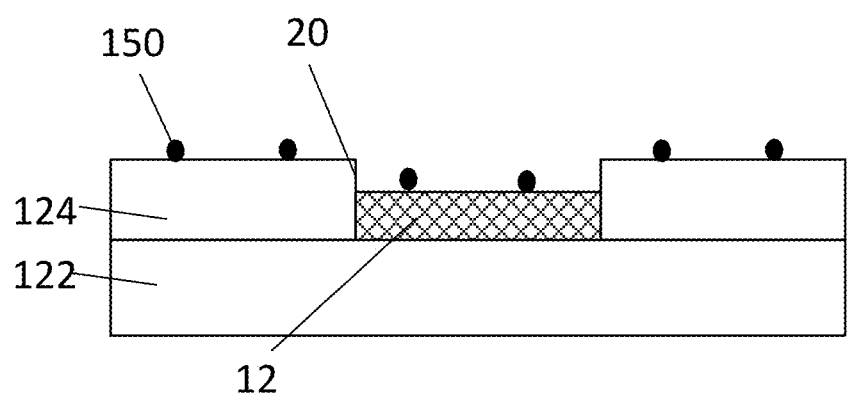
FIG. 9B shows a cross-sectional view taken along the line 9B-9B included in FIG. 9A.

Now, an example of a method for fabricating the cell potential measuring electrode assembly will be described. As shown in FIG. 9B, the insulating fibers 150 having cell compatibility are arranged on the insulating substrate 120 shown in FIG. 8B. This insulating substrate 120 comprises the conductive pattern 12 in the inside thereof. The insulating substrate 120 comprises a hole 20. A part of the conductive pattern 12 is exposed at the bottom of the hole 20. Then, the part of the conductive pattern 12 exposed at the bottom of the hole 20 is plated with metal. In this way, the cell potential measuring electrode assembly 100 shown in FIG. 3B is fabricated.

EXAMPLES

Hereinafter, the present invention will be described in more detail with reference to the following examples.

Inventive Example 1

Figure 5:
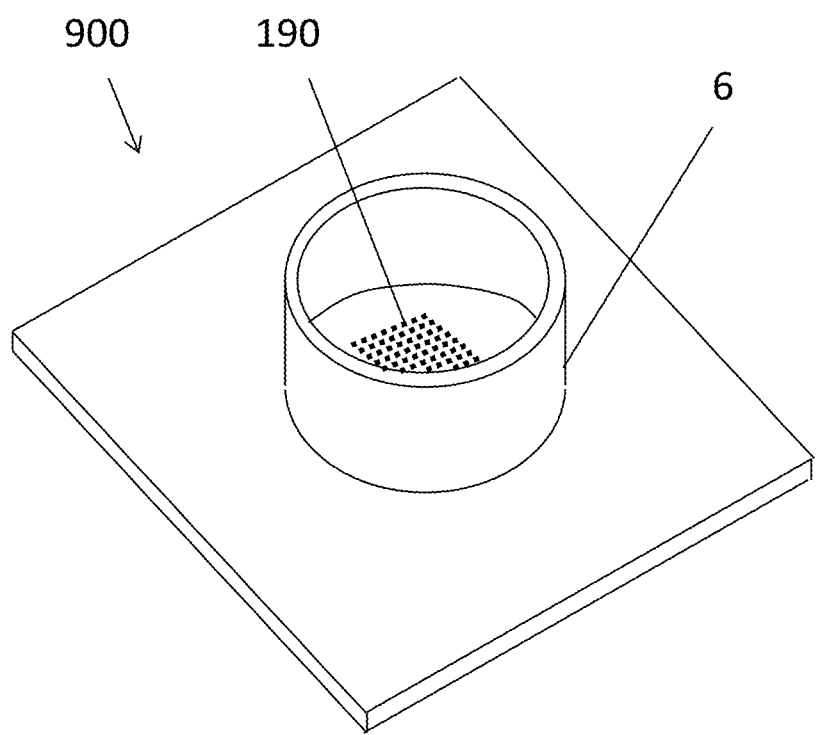
FIG. 5 shows a schematic view of a commercially-available cell potential measuring electrode assembly 900.

First, a cell potential measuring electrode assembly 900 shown in FIG. 5 was procured (from Alpha Med Scientific Inc., trade name: MED-P545A). This cell potential measuring electrode assembly 900 comprised sixty-four measurement electrodes 190 (i.e., eight columns×eight lines) in the inside of the cylindrical member 6. For more detail of this cell potential measuring electrode assembly 900, see U.S. Pat. No. 6,132,683, which is incorporated herein by reference. The cylindrical member 6 defines the chamber.

Figure 6:
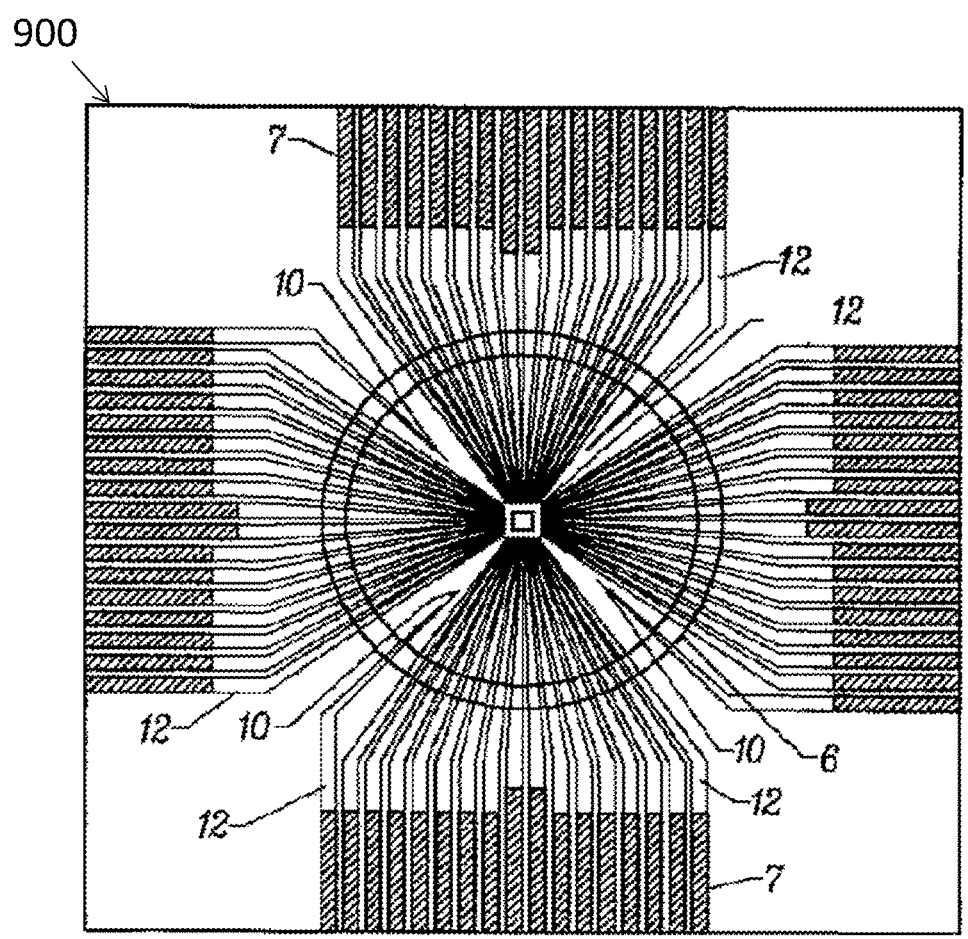
FIG. 6 shows a top view of the cell potential measuring electrode assembly 900.

FIG. 6 shows a top view of the cell potential measuring electrode assembly 900. The cell potential measuring electrode assembly 900 had sixty-eight electrodes 7 and conductive patterns 12 in the outside of the cylindrical member 6, as shown in FIG. 6. Each electrode 7 was electrically connected to one end of one of the conductive patterns 12. Among these electrodes 7, four electrodes 7 were the reference electrodes 10. The other ends of respective conductive patterns 12 electrically connected to the remaining sixty electrodes 7 were electrically connected to the measurement electrode 190 in the inside of the cylindrical member 6. In FIG. 5, the electrodes 7, the reference electrodes 10, and the conductive patterns 12 are omitted. In FIG. 6, the measurement electrodes 190 are omitted.

Figure 7A:
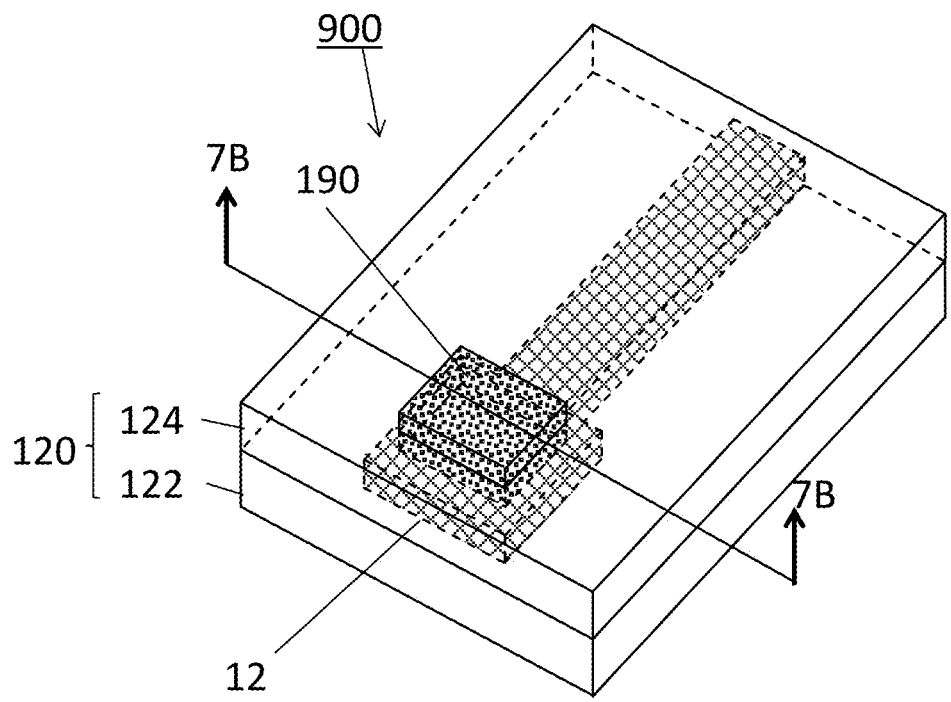
FIG. 7A shows a schematic view of one measurement electrode 110 included in the cell potential measuring electrode assembly 900.
Figure 7B:
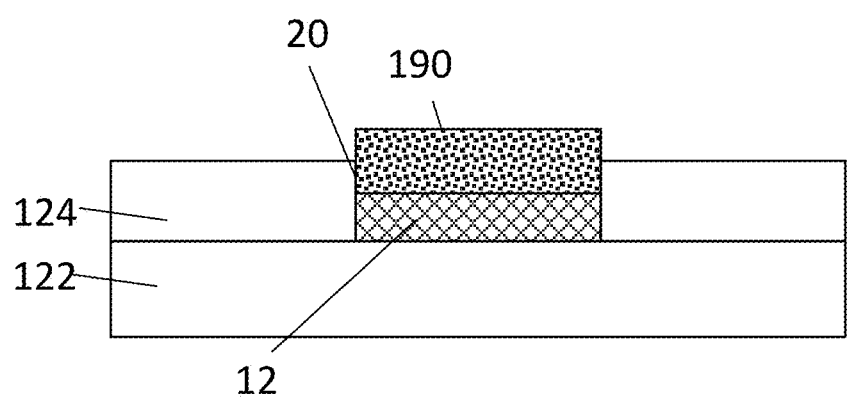
FIG. 7B shows a cross-sectional taken along the line 7B-7B included in FIG. 7A.

FIG. 7A shows a schematic view of one measurement electrode 110 included in the cell potential measuring electrode assembly 900. FIG. 7B shows a cross-sectional view taken along the line 7B-7B included in FIG. 7A. The cell potential measuring electrode assembly 900 comprised the first substrate 122 formed of glass, the second substrate 124 formed of an insulator, the conductive patterns 12 formed of indium tin oxide, and measurement electrodes 190 each formed of platinum black, as shown in FIG. 7A and FIG. 7B.

Figure 8A:
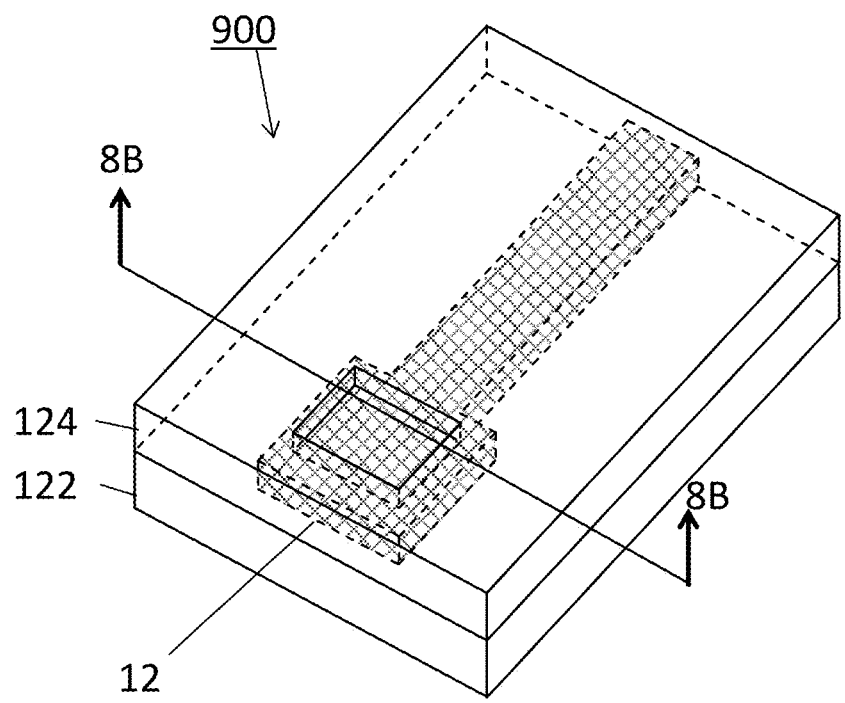
FIG. 8A shows a schematic view of one step included in a method for fabricating the cell potential measuring electrode assembly 100.

Water having a volume of approximately 2 milliliters was supplied to the inside of the cylindrical member 6. The measurement electrodes 190 were removed with a cotton swab. As shown in FIG. 8A and FIG. 8B, in this way, a part of the conductive pattern 12 formed of indium tin oxide was exposed at the bottom of the through-hole 20 provided to the second substrate 124. Subsequently, the cell potential measuring electrode assembly was dried naturally.

The cell potential measuring electrode assembly was subjected to a plasma surface treatment for two minutes at a RF power of 18 W using a plasma treatment device (available from HARRICK PLASMA, trade name: PDC-32G).

Meanwhile, procured was aluminum tape in which nanofibers made of polymethyl glutaric imide were formed on the surface thereof by an electrospinning method (available from Hitachi Maxell. Ltd., trade name: SLIONTEC). The nanofibers had a surface coverage of 50%.

Then, the aluminum tape having the nanofibers was arranged on the surface of the cell potential measuring electrode assembly so that the nanofibers were sandwiched between the aluminum tape and the conductive pattern 12. The aluminum tape having the nanofibers was impressed onto the surface of the second substrate 124 and on the surface of the parts of the conductive patterns 12 each exposed at the bottom of the through-holes 20. Then, the aluminum tape was removed. In this way, as shown in FIG. 9A and FIG. 9B, the nanofibers 150 were transcribed on the surface of the second substrate 124 and on the surface of the parts of the conductive patterns 12 each exposed at the bottom of the through-hole 20.

Finally, the parts of the conductive patterns 12 each exposed at the bottom of the through-hole 20 were plated with platinum black. Specifically, the parts were plated at a current density of 20 mA/cm$^2$ for two minutes using a plating solution. During the plating, the conductive patterns 12 were used as cathodes. The plating solution has the composition shown in Table 1. The measurement electrodes 110 were formed through such plating on the surface of the parts of the conductive patterns 12 each exposed at the bottom of the through-hole 20.

TABLE 1

| Composition | Chemical formula | Concentration |
| --- | --- | --- |
| Hexachloroplatinic (IV) acid | $H_2PtCl_6 \cdot 6H_2O$ | 1% |
| Lead acetate | $(CH_3COO)_2Pb \cdot 3H_2O$ | 0.01% |
| Hydrochloric acid | HCl | 0.0025% |

In this way, as shown in FIG. 3A and FIG. 3B, the cell potential measuring electrode assembly 100 according to the inventive example 1 was provided.

Then, impedance of the cell potential measuring electrode assembly according to the inventive example 1 was measured, while a sine wave having a frequency of 10-100 kHz and having a voltage of 1 volt was applied to the cell potential measuring electrode assembly according to the inventive example 1 using an impedance measurement device (available from NF Corporation, trade name: ZM2371).

Comparative Example 1

In the comparative example 1, the experiment similar to the inventive example 1 was conducted, except that the cell potential measuring electrode assembly 900 was subjected to the plasma surface treatment without removing the measurement electrodes 190 formed of platinum black, and that the conductive pattern 12 was not plated.

In other words, in the comparative example 1, the cell potential measuring electrode assembly 900 comprising the measurement electrodes 190 formed of platinum black was subjected to the plasma surface treatment at an RF power of 18 W for two minutes using the plasma treatment device. Then, the aluminum tape having nanofibers was impressed onto the surface of the cell potential measuring electrode assembly. The aluminum tape having nanofibers was removed to transcribe the nanofibers 150 onto surfaces of the second substrate 124 and the measurement electrodes 190. In this way, the cell potential measuring electrode assembly according to the comparative example 1 was provided.

Reference Example 1

In the reference example 1, the cell potential measuring electrode assembly 900 purchased from Alpha Med Scientific Inc. was used without any change for the impedance measurement. In other words, in the reference example 1, the measurement electrodes 190 each formed of platinum black were not removed. The cell potential measuring electrode assembly 900 was not subjected to the plasma treatment. The nanofibers were not transcribed onto the cell potential measuring electrode assembly 900, either.

Figure 14:
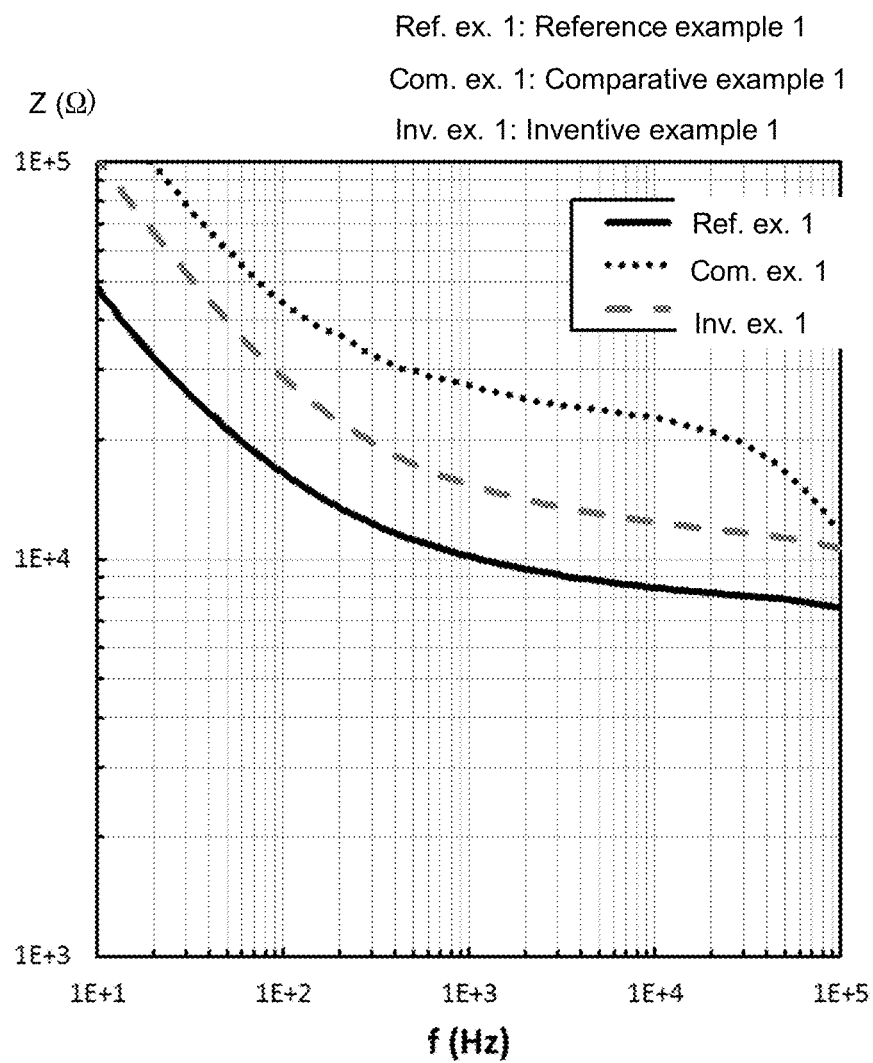
FIG. 14 shows impedance measurement results of the cell potential measuring electrode assemblies 900 according to the inventive example 1, the comparative example 1, and the reference example 1.

FIG. 14 shows the results of the impedance measurement of the cell potential measuring electrode assemblies according to the inventive example 1, the comparative example 1, and the reference example 1.

As understood from FIG. 14, the cell potential measuring electrode assembly 100 according to the inventive example 1 has lower impedance than the cell potential measuring electrode assembly according to the comparative example 1. The cell potential measuring electrode assembly 900 according to the reference example 1 has the lowest impedance, however, note that the cell potential measuring electrode assembly 900 according to the reference example 1 does not have a nanofiber which is required for the cell maturity.

Inventive Example 2

Figure 10:
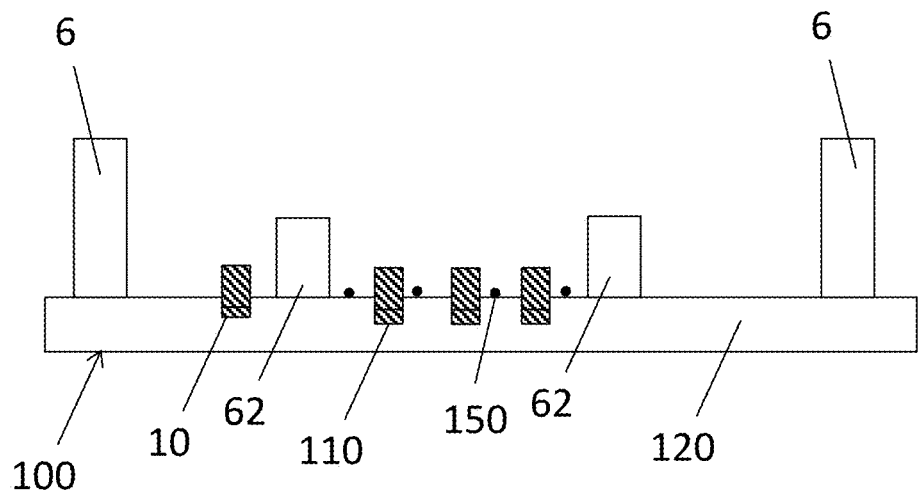
FIG. 10 shows a cross-sectional view of one step included in a method for using the cell potential measuring electrode assembly 100.

In the inventive example 2, the electric potential change of the cardiomyocyte was measured using the cell potential measuring electrode assembly 100 according to the inventive example 1. Specifically, iPS differentiated cardiomyocytes derived from human (available from iPS Academia Japan, Inc., trade name: iCell Cardiomycytes) were used. Pursuant to the protocol described in the manual attached to iCell Cardiomycytes, a culture fluid containing iPS differentiation cardiomyocytes derived from human was prepared. Then, as shown in FIG. 12, the culture fluid 182 was supplied on the cell potential measuring electrode assembly 100 according to the inventive example 1. The concentration of the iPS differentiated cardiomyocytes 180 on the cell potential measuring electrode assembly 100 was $1.5 \times 10^4$ cell/mm$^2$. The insulating ring 62 was used in the inventive example 2 as shown in FIG. 10 to FIG. 12.

The electric potential difference between the reference electrode 10 and the measurement electrode 110 was measured using a cell electric potential measurement device (from Alpha Med Scientific Inc., trade name: MED-64). In this way, the electric potential change of the cells 180 was measured.

Figure 15:
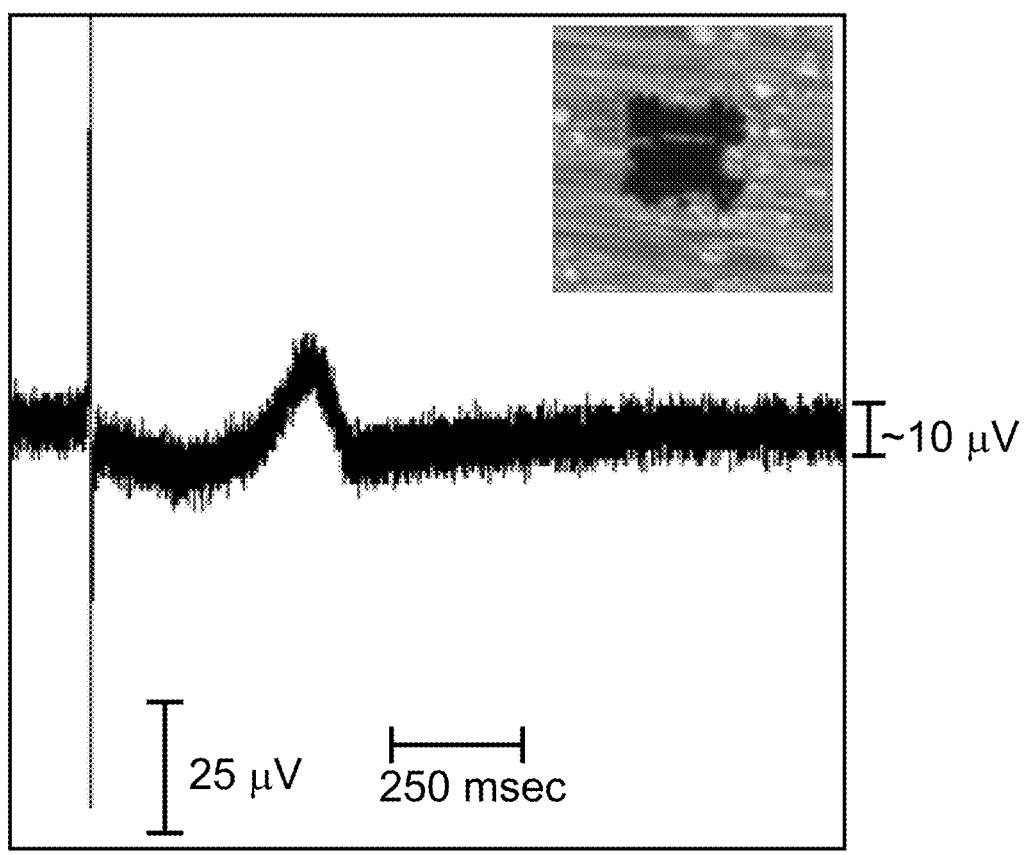
FIG. 15 is a graph showing a measurement result in the inventive example 2.

FIG. 15 is a graph showing the result of the measurement in the inventive example 2.

Comparative Example 2

Figure 16:
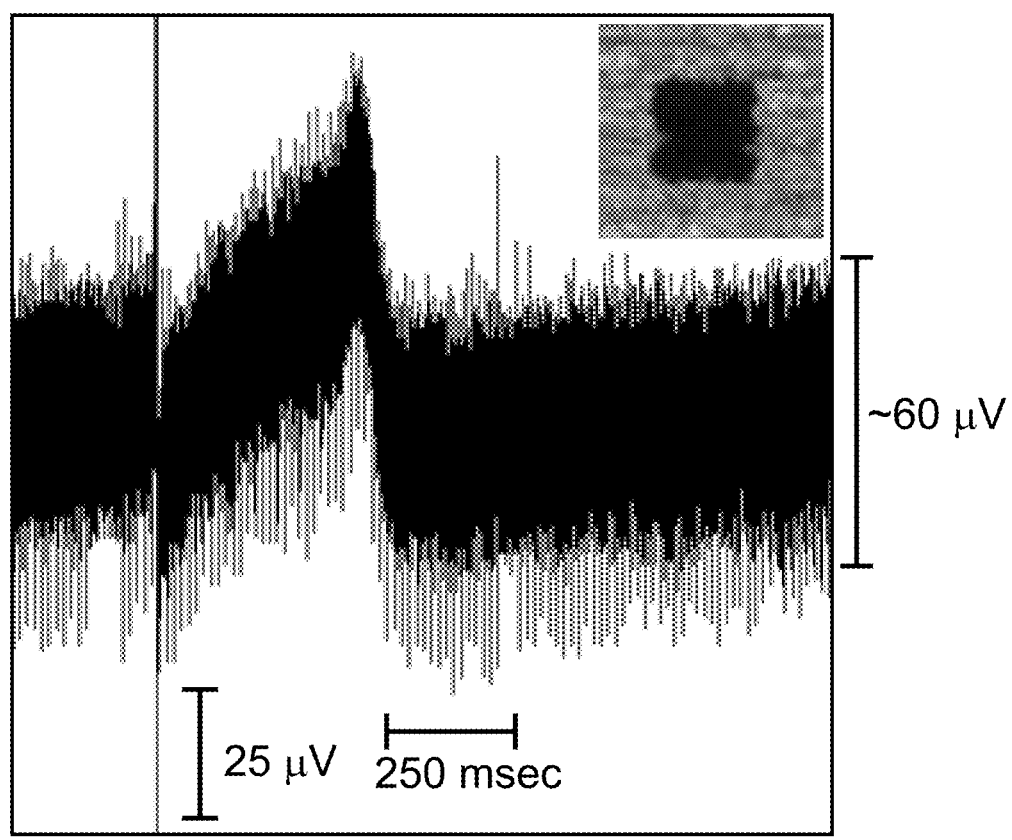
FIG. 16 is a graph showing a measurement result in the comparative example 2.
Figure 17:
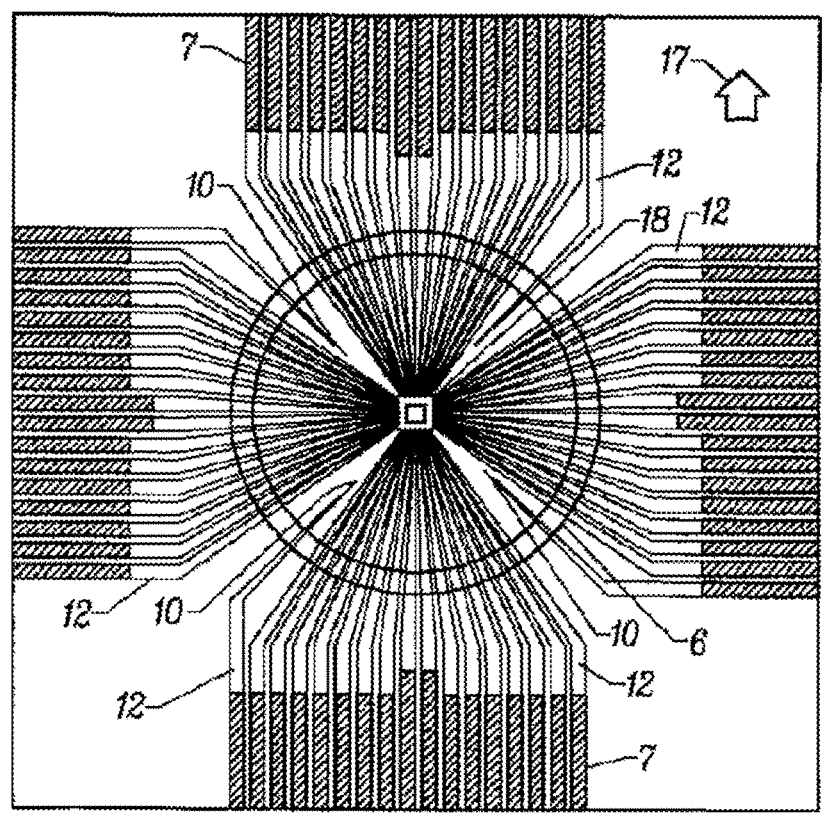
FIG. 17 shows a cell potential measuring electrode assembly disclosed in U.S. Pat. No. 6,132,683.

In the comparative example 2, an experiment similar to the inventive example 2 was conducted, except that the cell potential measuring electrode assembly according to the comparative example 1 was used in place of the cell potential measuring electrode assembly 100 according to the inventive example 1. FIG. 16 is a graph showing the result of the measurement in the comparative example 2.

As is clear from FIG. 15 and FIG. 16, the measurement noise was a low value of approximately 10 microvolts in the inventive example 2; however, the measurement noise was a high value of approximately 60 microvolts in the comparative example 2. As just described, a significantly high noise occurs in a case where the insulating fiber 150 is arranged on the front surface 110f of the measurement electrode 110. For this reason, it is required for a significantly small noise that the insulating fiber 150 is arranged on the back surface 110b of the measurement electrode 110.

INDUSTRIAL APPLICABILITY

The present invention can be used for drug discovery screening.

REFERENTIAL SIGNS LIST

100 Cell potential measuring electrode assembly
110 Measurement electrode
110a Front surface
110b Back surface
6 Cylindrical member
7 Electrode
10 Reference electrode
11 Reference electrode
12 Conductive pattern
20 Through-hole
120 Insulating substrate
122 First substrate
124 Second substrate
150 Insulating fiber
180 Cell
62 Insulating ring

The invention claimed is:

1. A cell potential measuring electrode assembly comprising:
    an insulating substrate;
    a conductive pattern arranged in the insulating substrate;
    an insulating fiber having cell compatibility; and
    a measurement electrode,
    wherein the insulating fiber is arranged on the insulating substrate;
    the measurement electrode has a front surface and a back surface;
    the back surface of the measurement electrode is in contact with the conductive pattern; and
    the insulating fiber is not arranged on the front surface of the measurement electrode.

2. The cell potential measuring electrode assembly according to claim 1, wherein the insulating fiber is arranged on the conductive pattern in a cross section along a thickness direction of the insulating substrate.

3. The cell potential measuring electrode assembly according to claim 2, wherein the insulating fiber is in contact with both the conductive pattern and the measurement electrode.

4. The cell potential measuring electrode assembly according to claim 1, comprising a plurality of the insulating fibers.

5. The cell potential measuring electrode assembly according to claim 4, comprising a plurality of the conductive patterns; and a plurality of the measurement electrodes.

6. The cell potential measuring electrode assembly according to claim 4, wherein
    the plurality of the insulating fibers are linear; and
    the plurality of the insulating fibers are arranged along one direction.

7. The cell potential measuring electrode assembly according to claim 1, wherein
    the insulating substrate comprises a first substrate and a second substrate which is stacked on the first substrate;
    the conductive pattern is formed on the first substrate;
    the second substrate comprises a through-hole;
    a part of the measurement electrode is embedded in the through-hole;
    the measurement electrode is connected electrically to the conductive pattern at a bottom of the through-hole; and
    the insulating fiber is arranged on the second substrate.

8. The cell potential measuring electrode assembly according to claim 7, wherein the insulating fiber is arranged on the conductive pattern in a cross section along a thickness direction of the insulating substrate.

9. The cell potential measuring electrode assembly according to claim 8, wherein the insulating fiber is in contact with both the conductive pattern and the measurement electrode.

10. The cell potential measuring electrode assembly according to claim 7, comprising a plurality of the insulating fibers.

11. The cell potential measuring electrode assembly according to claim 10, comprising a plurality of the conductive patterns; and a plurality of the measurement electrodes.

12. The cell potential measuring electrode assembly according to claim 10, wherein
the plurality of the insulating fibers are linear; and
the plurality of the insulating fibers are arranged along one direction.

13. The cell potential measuring electrode assembly according to claim 1, wherein the measurement electrode is formed of platinum.

14. The cell potential measuring electrode assembly according to claim 1, wherein the insulating fiber is unfixed on the insulating substrate.

15. The cell potential measuring electrode assembly according to claim 1, wherein the insulating fiber is formed of a polymer selected from the group consisting of polystyrene, polycarbonate, polymethylmethacrylate, polyvinyl chloride, polyethylene terephthalate, polyamide, polymethyl glutaric imide and polylactic acid.

16. The cell potential measuring electrode assembly according to claim 1, wherein the cell potential measuring electrode assembly according is a cardiomyocyte potential measuring electrode assembly.

17. A method for measuring an electric potential change of a plurality of cells, comprising:
(a) preparing a cell potential measuring electrode assembly; wherein
the cell potential measuring electrode assembly comprises:
an insulating substrate;
a conductive pattern arranged in the insulating substrate;
an insulating fiber having cell compatibility; and
a measurement electrode,
the insulating fiber is arranged on the insulating substrate;
the measurement electrode has a front surface and a back surface;
the back surface of the measurement electrode is in contact with the conductive pattern;
the insulating fiber is not arranged on the front surface of the measurement electrode; and
the cell potential measuring electrode assembly comprises a reference electrode on a surface thereof;
(b) supplying a culture fluid containing the plurality of the cells on the insulating substrate so as to be in contact with the measurement electrode and the insulating fiber; and
(c) measuring an electric potential difference between the reference electrode and the measurement electrode as the electric potential change of the plurality of the cells.

18. The method according to claim 17, further comprising:
leaving the plurality of the cells at rest between the step (b) and the step (c).

19. The method according to claim 17, wherein the plurality of the cells are cardiomyocytes.

20. The method according to claim 17, wherein the insulating fiber is arranged on the conductive pattern in a cross section along a thickness direction of the insulating substrate.

21. The method according to claim 20, wherein the insulating fiber is in contact with both the conductive pattern and the measurement electrode.

22. The method according to claim 17, comprising a plurality of the insulating fibers.

23. The method according to claim 22, comprising a plurality of the conductive patterns; and a plurality of the measurement electrodes.

24. The method according to claim 22, wherein
the plurality of the insulating fibers are linear; and
the plurality of the insulating fibers are arranged along one direction.

25. The method according to claim 17, wherein
the insulating substrate comprises a first substrate and a second substrate which is stacked on the first substrate;
the conductive pattern is formed on the first substrate;
the second substrate comprises a through-hole;
a part of the measurement electrode is embedded in the through-hole;
the measurement electrode is connected electrically to the conductive pattern at a bottom of the through-hole; and
the insulating fiber is arranged on the second substrate.

26. The method according to claim 25, wherein the insulating fiber is arranged on the conductive pattern in a cross section along a thickness direction of the insulating substrate.

27. The method according to claim 26, wherein the insulating fiber is in contact with both the conductive pattern and the measurement electrode.

28. The method according to claim 25, comprising a plurality of the insulating fibers.

29. The method according to claim 28, comprising a plurality of the conductive patterns; and a plurality of the measurement electrodes.

30. The method according to claim 28, wherein
the plurality of the insulating fibers are linear; and
the plurality of the insulating fibers are arranged along one direction.

31. The method according to claim 17, wherein the measurement electrode is formed of platinum.

32. The method according to claim 17, wherein the insulating fiber is unfixed on the insulating substrate.

33. A method for measuring an electric potential change of a plurality of cells, comprising:
(a) preparing a cell potential measuring electrode assembly; wherein
the cell potential measuring electrode assembly comprises:
a conductive pattern arranged in the insulating substrate;
an insulating fiber having cell compatibility; and
a measurement electrode,
the insulating fiber is arranged on the insulating substrate;
the measurement electrode has a front surface and a back surface;
the back surface of the measurement electrode is in contact with the conductive pattern; and
the insulating fiber is not arranged on the front surface of the measurement electrode;
(b) supplying a culture fluid containing the plurality of the cells on the insulating substrate so as to be in contact with the measurement electrode and the insulating fiber; and
(c) measuring an electric potential difference between a reference electrode and the measurement electrode as the electric potential change of the plurality of the cells, wherein
the method further comprises a step of bringing the reference electrode into contact with the culture fluid between the step (b) and the step (c).

* * * * *